United States Patent [19]

Carter

[11] Patent Number: 4,683,748

[45] Date of Patent: * Aug. 4, 1987

[54] METHOD AND APPARATUS FOR MEASURING DYNAMIC FLUID FLOW RATE

[75] Inventor: Garry L. Carter, Racine, Wis.

[73] Assignee: Medical Engineering Corp., Racine, Wis.

[*] Notice: The portion of the term of this patent subsequent to May 20, 2003 has been disclaimed.

[21] Appl. No.: 829,597

[22] Filed: Feb. 13, 1986

Related U.S. Application Data

[63] Continuation of Ser. No. 666,358, Oct. 30, 1984, Pat. No. 4,589,280, which is a continuation-in-part of Ser. No. 447,759, Dec. 8, 1982, abandoned.

[51] Int. Cl.$^4$ ............................................. G01F 3/38
[52] U.S. Cl. .................................... 73/226; 128/760
[58] Field of Search ................ 73/222, 223, 226, 299, 73/216, 861; 364/510; 128/760, 761, DIG. 12; 604/246, 247, 248

[56] References Cited

U.S. PATENT DOCUMENTS

| | | | |
|---|---|---|---|
| Re. 30,607 | 5/1981 | Manschot et al. | 128/762 |
| 2,814,950 | 12/1957 | Lawlor | 73/216 |
| 3,726,140 | 4/1973 | Barbee | 73/299 |
| 3,919,455 | 11/1975 | Sigdell et al. | 73/226 |
| 3,949,745 | 4/1976 | Howell | 128/214 C |
| 3,986,398 | 10/1976 | Laymance | 73/299 |
| 4,000,649 | 1/1977 | Hanifl | 73/219 |
| 4,020,690 | 5/1977 | Samuels et al. | 73/299 |
| 4,051,431 | 9/1977 | Wurster | 324/61 R |
| 4,084,435 | 4/1978 | Weik et al. | 73/299 |
| 4,085,616 | 4/1978 | Patel et al. | 73/215 |
| 4,099,412 | 7/1978 | Nehrbass | 73/209 |
| 4,187,722 | 2/1980 | Layton | 73/229 |
| 4,200,112 | 4/1980 | McWhorter | 128/761 |
| 4,241,017 | 12/1980 | Balistreri et al. | 422/58 |
| 4,285,245 | 8/1981 | Kennedy | 73/861 |
| 4,301,813 | 11/1981 | Merry et al. | 128/762 |
| 4,343,316 | 8/1982 | Jespersen | 128/771 |
| 4,355,638 | 10/1982 | Iwatschenko et al. | 128/214 |
| 4,395,918 | 8/1983 | Wilson | 73/861 |
| 4,458,539 | 7/1984 | Bilstad et al. | 73/296 X |
| 4,589,280 | 5/1986 | Carter | 73/226 |

FOREIGN PATENT DOCUMENTS 2031158  4/1980  United Kingdom.

OTHER PUBLICATIONS

"Uroflometry in Urological Diagnosis", by Joseph J. Kaufman, M.D. *California Medicine*, vol. 95, Aug. 1961, pp. 100–103.

"Analysis of Micturition, A New Method of Recording the Voiding of the Bladder", *Acta Chirargica Scandinavica* (1956), von Garrelts, B., pp. 326–340.

"A New Uroflowmeter For Routine Clinical Use", by N. J. Randall, *Biomedical Engineering*, vol. 10, No. 1., Jan. 1975, pp. 21–24.

*Primary Examiner*—James L. Rowland
*Assistant Examiner*—Brian R. Tumm
*Attorney, Agent, or Firm*—Quarles & Brady

[57] ABSTRACT

A method and apparatus for measuring a dynamic flow rate of a bodily fluid in which the rate of flow is constantly changing includes an inlet to a chamber where flow accumulates. The accumulating fluid is in communication with the base of a sealed vertical column of air. An air pressure transducer in the upper portion of the column of air measures the pressure exerted upon the air by the accumulated fluid. The air pressure corresponds to the volume of accumulated fluid and is manipulated to yield a running indication of the flow rate. The chamber is automatically drained by a drainage conduit when the fluid reaches an upper operating level to reset the apparatus to a lower operating level to be ready to resume taking meaurements.

3 Claims, 3 Drawing Figures

4,683,748

METHOD AND APPARATUS FOR MEASURING DYNAMIC FLUID FLOW RATE

This is a continuation of application Ser. No. 666,358 filed Oct. 30, 1984, U.S. Pat. No. 4,589,280 issued May 20, 1986, which application was a continuation-in-part of application Ser. No. 447,759 filed Dec. 8, 1982, now abandoned.

Field Of The Invention

This invention relates to fluid flow measurement and more particularly to fluid flow measurement in medical applications.

BACKGROUND OF THE INVENTION

Diagnosis of kidney and urinary tract infections is often facilitated by a knowledge of the patient's urinary flow rate. Urinary flow rate data is particularly important in critical care situations, and in particular when the patient has just undergone surgery since the patient may not be conscious and able to verbalize any symptoms. In critical care situations, urine is usually continuously drained from the body via a Foley type catheter and the urine output is usually determined by visually observing the amount of urine drained from the patient via the catheter into a drainage receptacle.

Examples of prior art drainage receptacles for enabling the quantity of urine drained via a Foley type catheter to be determined are found in U.S. Pat. Nos. 4,301,813, 4,095,589, 4,085,616 and 4,000,649. Each of the prior art drainage receptacles described in the above listed patents includes a transparent urine receiving chamber having a graduated scale thereon for indicating the quantity of urine entering the chamber. The urine flow rate is determined in such devices by observing the quantity of urine entering the chamber of the drainage receptacle over a period of time.

While the prior art devices are satisfactory for this purpose, there are several disadvantages associated with measuring urine in this manner. The most obvious disadvantage is that the urine flow is detected visually. This requires either a nurse, a doctor or a technician to observe the patient for a set period of time. In practice, a nurse generally records the volume of urine at 15 minute intervals. However, inaccuracies may arise due to failure to maintain an exact interval between observations. In addition, an exact measurement may not always be obtained due to the imprecisions in reading the drainage receptacle scale. More importantly, the use of prior art urine flow measuring techniques do not provide an instantaneous measure of excessive urine output unless the nurse, doctor or technician is present to observe the excessive urine output.

SUMMARY OF THE INVENTION

The invention provides a method and apparatus for measuring a dynamic fluid flow rate in which the rate of flow is constantly changing. The method includes accumulating the fluid flow and providing communication between the accumulating fluid and the base of a sealed column of air so that the fluid produces an air pressure in the column corresponding to the volume of accumulated fluid. The air pressures in the column of air are measured over time and are converted into an indication of the flow rates over time. This method is particularly useful with bodily fluids because the measuring device never contacts the bodily fluid. Contamination of the measuring device is thereby avoided.

In a preferred aspect of the method, the air pressures are measured at regular time intervals. The pressures are then converted to corresponding volumes and the differences between successive volumes are divided by the time interval. This yields the average flow rates over the corresponding time intervals.

The apparatus operates according to the method to provide a running indication of the dynamic flow rate of a bodily fluid. A unitary container is used in the apparatus which includes a chamber for accumulating the bodily fluid and inlet means for admitting the bodily fluid into the chamber. The container also includes a sealed vertical measurement conduit for enclosing the column of air. The measurement conduit shares a wall in common with the chamber and is in communication with the chamber through an opening in the common wall at the base of the conduit. The measuring port of an air pressure transducer is mountable in the upper portion of the measurement conduit and means provide communication between the interior of the chamber and a gauge port of the air pressure transducer. Drainage means are also provided for draining accumulated bodily fluid from the chamber. This construction provides a container for the apparatus which can be inexpensively manufactured so as to allow disposal it after use.

In a preferred form of the unitary container for the apparatus, the means for providing communication between the interior of the chamber and the gauge port of the air pressure transducer includes a vent in the upper portion of the chamber. Thereby, the gauge port and the interior of the chamber are in communication by both being exposed to the atmosphere.

With the chamber vented to the atmosphere, the drainage means can be a vertical drainage conduit having a wall in common with the chamber. The drainage conduit is in communication with the chamber through the common wall above where the measurement conduit is in communication with the chamber. The drainage conduit also has an upper end below the air pressure transducer mounting means, the upper end being sealable to a downwardly depending tube. This drainage means acts to repeatedly siphon the accumulated bodily fluid from the chamber from an upper operating level at the height of the upper end of the drainage conduit to a lower operating level at the height where the drainage conduit is in communication with the chamber. Thereby, the chamber will be automatically reset so that the apparatus will be ready to resume flow rate measurements.

It is an object of the invention to provide a method and apparatus for measuring a constantly and quickly changing rate of flow of a bodily fluid such as urine.

It is yet another object of the invention to provide a method and apparatus for measuring a dynamic rate of bodily fluid flow electrically.

It is yet another object of the invention to provide a method and apparatus for measuring a dynamic rate of bodily fluid flow in which the parts in contact with the bodily fluid are inexpensive to manufacture so as to make disposal after use economical.

It is yet another object of the invention to provide a method and apparatus for measuring a dynamic rate of bodily fluid flow which is automatically reset to be ready to resume measurement.

Other objects and advantages will become apparent from the following detailed description and from the drawings.

DETAILED DESCRIPTION OF THE PREFERRED EMBODIEMENTS

Figure 1:
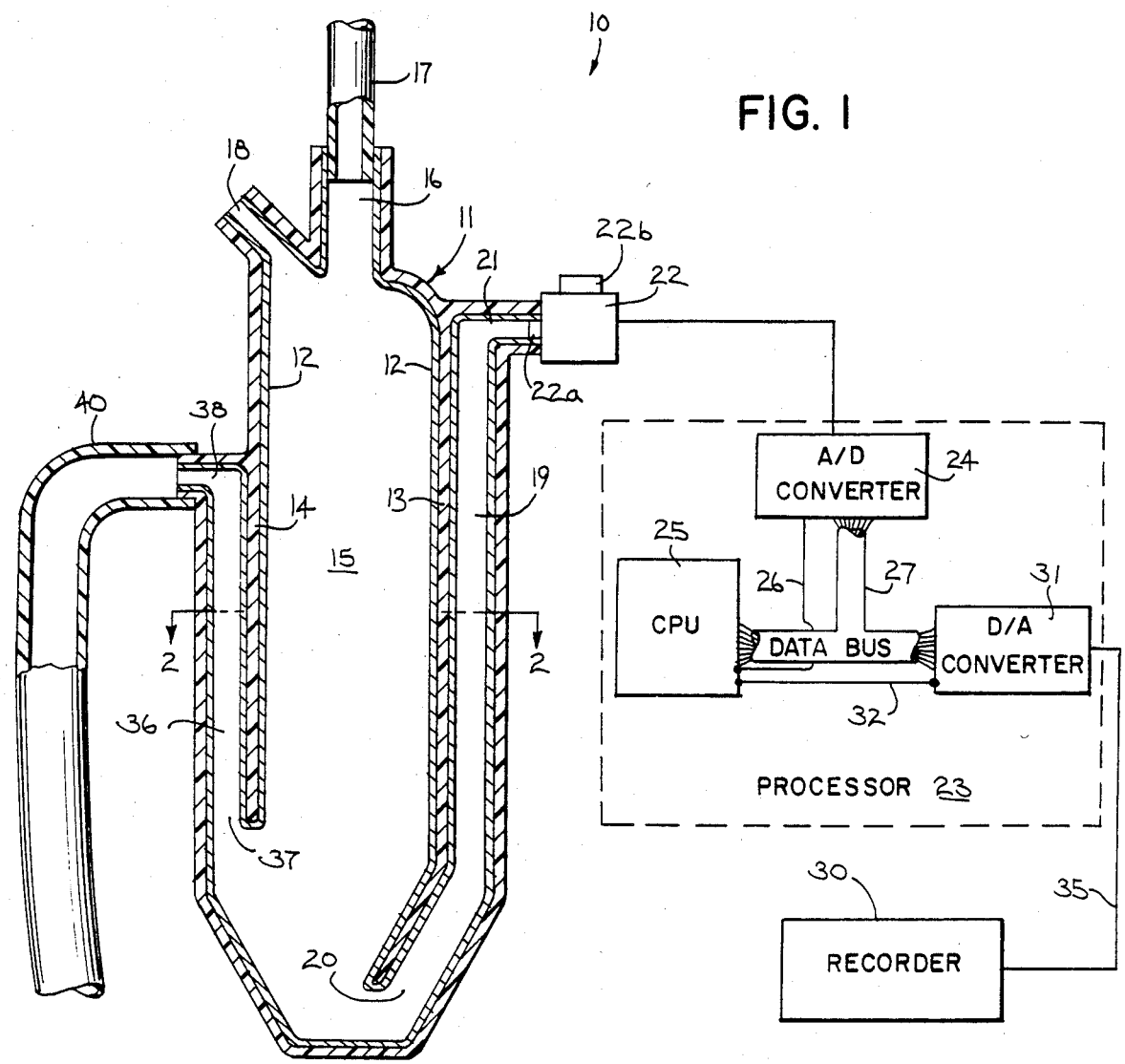
FIG. 1 is a block diagram of a fluid flow meter apparatus of the present invention.
Figure 2:
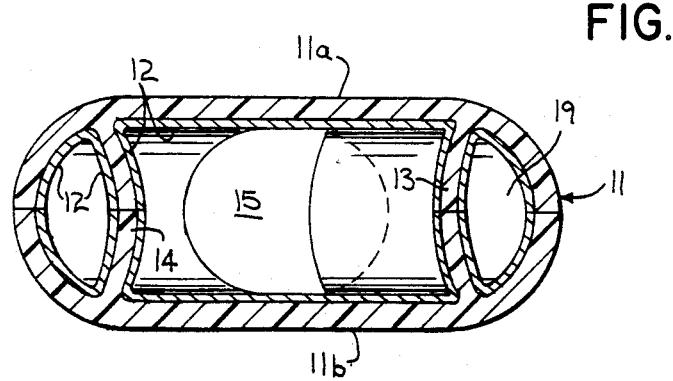
FIG. 2 is a cross-sectional view of the container of the fluid flow meter apparatus of FIG. 1 taken along the plane of the line 2—2 thereof.

FIG. 1 illustrates a fluid flow meter 10 of the present invention which includes a container 11. Referring also to FIG. 2, the container 11 is made up of two rigid wall sections 11a and 11b which are joined at their edges. The wall sections 11a and 11b are preferably made of a transparent resinous material such as polystyrene. The interior surfaces of the wall sections 11a and 11b are coated with a hydrophilic coating 12. In practice, the hydrophilic coating 12 comprises a coating sold under the trade designation "HYDROMER" which is a polyurethane polyvinyl pyrollidone interpolymer manufactured by Biosearch, Whitehouse, New Jersey. Note that in some applications it may be desirable to add a hydrophilic additive directly to the resinous material of the wall sections so as to avoid the need to coat the surfaces with a hydrophilic coating.

The wall sections 11a and 11b provide two interior baffles 13 and 14. The baffles 13 and 14 along with the exterior walls of the container 11 make up an interior chamber which defines a cavity 15. The chamber has an upper portion with an inlet opening 16. The inlet opening 16 is suitable to be connected to a tube 17 that carries the liquid, the flow rate of which is to be measured, into the cavity 15. The tube 17 may be connected to a catheter (not shown) such as a Foley-type catheter, which is in-dwelling in a patient so that the 1:quid, such as urine, can flow from the patient through the catheter and the connecting tube 17 and into the container 11. The upper portion of the interior chamber is also provided with a vent opening 18, preferably above the inlet 14. In the container 11, the vent opening 18 admits air at atmospheric pressure into the interior cavity 15.

The baffle 13 and the right hand portions of the exterior walls of the container 11 make up a first conduit which defines a first passageway 19. The passageway 19 extends for substantially the entire height of the cavity 15 and opens into the cavity 15 well below the inlet and vent openings at a lower opening 20 which is relatively closely adjacent to the bottom of the container 11. The passageway 19 also has an upper opening 21 which opens to the exterior of the container 11. The upper opening 21 is thereby in communication with the cavity 15 below the inlet opening 16 and the vent opening 18.

The upper opening 21 is suitable to easily mount a pressure transducer 22 in operative relationship so that the upper opening 21 is sealed by the transducer 22 and the transducer 22 can measure the air pressure within the passageway 19. The transducer 22 provides an electrical signal in accordance with the air pressure in the passageway 19. The transducer should be capable of following the air pressure as closely as possible to provide a near instantaneous indication thereof. Note that this arrangement shields the pressure transducer 22 from urine contamination so that it need not be cleaned and is reuseable.

Either gauge or absolute pressure could be sensed by the pressure transducer 22. However, as will become clear from the following description, it is preferable to sense gauge pressure since atmospheric pressure acts on the liquid within the cavity 15. If absolute pressure were measured, the atmospheric pressure would be taken account of in the processing required to convert the pressure signal into a volume. A transducer 22 which was found suitable in practice is the transducer sold under the trade designation Microswitch No. 142PCO1G. This transducer has a measuring port 22a and a gauge port 22b. In practice, the measuring port 22a is mounted to the opening 21 and the gauge port 22b is left open to the atmosphere to measure gauge pressure.

As liquid is admitted into the cavity 15 through the inlet opening 16, the level of liquid within the cavity rises. When the level of liquid in the cavity is below the lower opening 20, the pressure in the passageway 19 will be equal to atmospheric pressure due to the atmospheric vent 18. However, when the level of liquid rises above the opening 20, the passageway 19 becomes sealed from atmospheric pressure by the liquid. As the level of liquid in the cavity 15 rises above the opening 20, some of the liquid will enter the passageway 19 thereby compressing the air in the passageway and the air pressure in the passageway 19 will rise. The air pressure within the passageway 19 will depend upon the height of the liquid within the cavity 15 above the opening 20 which, in turn, is dependent upon the volume of the liquid within the container 11. Therefore, any given volume of liquid within the container 11 will produce a corresponding air pressure within the passageway 19.

While the air pressure within the passageway 19 can be used to determine the volume of liquid within the container 11, it can also be applied to determine the rate of change of the volume of liquid within the container, which equals the flow rate into the container. Designating the volume of liquid within the container as V, the flow rate into the container as F and time as t, the flow rate is related to the change in volume, or $\Delta V$, by the following relationship:

$$F = \Delta V / \Delta t$$

so that $$\Delta V = F \Delta t.$$

Now, designating the area occupied by the free surface (the surface exposed to atmospheric pressure) of the liquid within the container 11 by A, and assuming A to be constant for the height of the container above the opening 20 to simplify the analysis, and designating the height of the liquid level above the opening 20 by h, the change in volume $\Delta V$ is related to the change in height $\Delta h$ as follows:

$$\Delta V = A \Delta h,$$

therefore $A \Delta h = F \Delta t$ so that $$\Delta h / \Delta t = F / A.$$

$\Delta V$ is not exactly equal to $A \Delta h$ because as the level of the liquid surface rises, some of the liquid will enter the passageway 21 to further compress the air therein. This introduces an approximation into the analysis but can be made negligible if the cross sectional area of the passageway 19 is small compared to the cross sectional area of the free surface of the liquid. Also, the error attributable to this approximation can be eliminated by the processing techniques explained below.

The rate of change of the height of the liquid level is represented by $\Delta h/\Delta t$. Therefore if A is substantially constant, it is shown that the rate of change of the height of the liquid level within the container 11 is directly proportional to the flow rate, F. Since the air pressure in the passageway 19 varies in accordance with the height of liquid within the cavity 15, the rate of change of the air pressure within the passageway 19 can be used as an indication of the flow rate into the cavity 15.

As previously mentioned, the output signal of the transducer 22 represents the instantaneous air pressure within the passageway 19. This signal could be input to a strip chart recorder or other output means to provide a graphical depiction of the pressure within the passageway 19 over a period of time. Since the graph would depict the pressure over time, one could get an indication of the rate of change of the pressure and therefore of the rate of change of the volume in the container 11 at a given instant by observing and/or measuring the slope of the graph at that instant.

Also, as previously mentioned, the output signal of the transducer 22, which is representative of the air pressure within the passageway 19, can be used to determine the height of liquid within the container 11 and can therefore also be used to determine the flow rate into the container. The exact relation between the air pressure in the passageway 19 and the height of the free surface of the liquid above the opening 20 is complicated by the fact that air is a compressible gas so that a change in the height of the free surface of the liquid causes some of the liquid to enter the passageway 19. While this complicates the relationship, the relationship is derivable and once derived, could be used to convert the air pressure in the passageway 19 into the height of the free surface or into the volume of the liquid within the container. The derived height or volume function could then be differentiated with respect to time to determine the flow rate.

However, it is not necessary to derive the relationship between the air pressure in the passageway 19 and the height or volume of the liquid within the container 11. It is not necessary because any volume of liquid of a given density within the container 11 which has a free surface above the opening 20 produces an air pressure within the passageway 19 which is repeatable. That is, for a known volume of liquid within the container 11, the air pressure within the passageway 19 can be experimentally measured. This can be repeated for many different known volumes of liquid and the resulting air pressures can be measured and recorded. Then later, when the volume within the container of the same liquid or of a liquid with substantially the same density is desired to be determined, the air pressure in the passageway 19 can be measured and compared with the earlier experimentally obtained results to obtain the volume of the liquid. This can be done for a series of unknown volumes and the resulting volume-time function can then be differentiated, such as by measuring the slope of the function at a given time, to yield the flow rate.

While this method of manually determining the flow rate is possible, it is tedious and time consuming. Therefore, a processor 23 is provided to convert the pressure transducer output signal into the flow rate. The pressure transducer 22 is connected to an analog to digital converter 24 which converts the pressure transducer output signal into a digital signal which is suitable to be input to a central processing unit 25. The central processing unit 25 is programmed to convert the digitized pressure signal into a flow rate and to output the flow rate.

Figure 3:
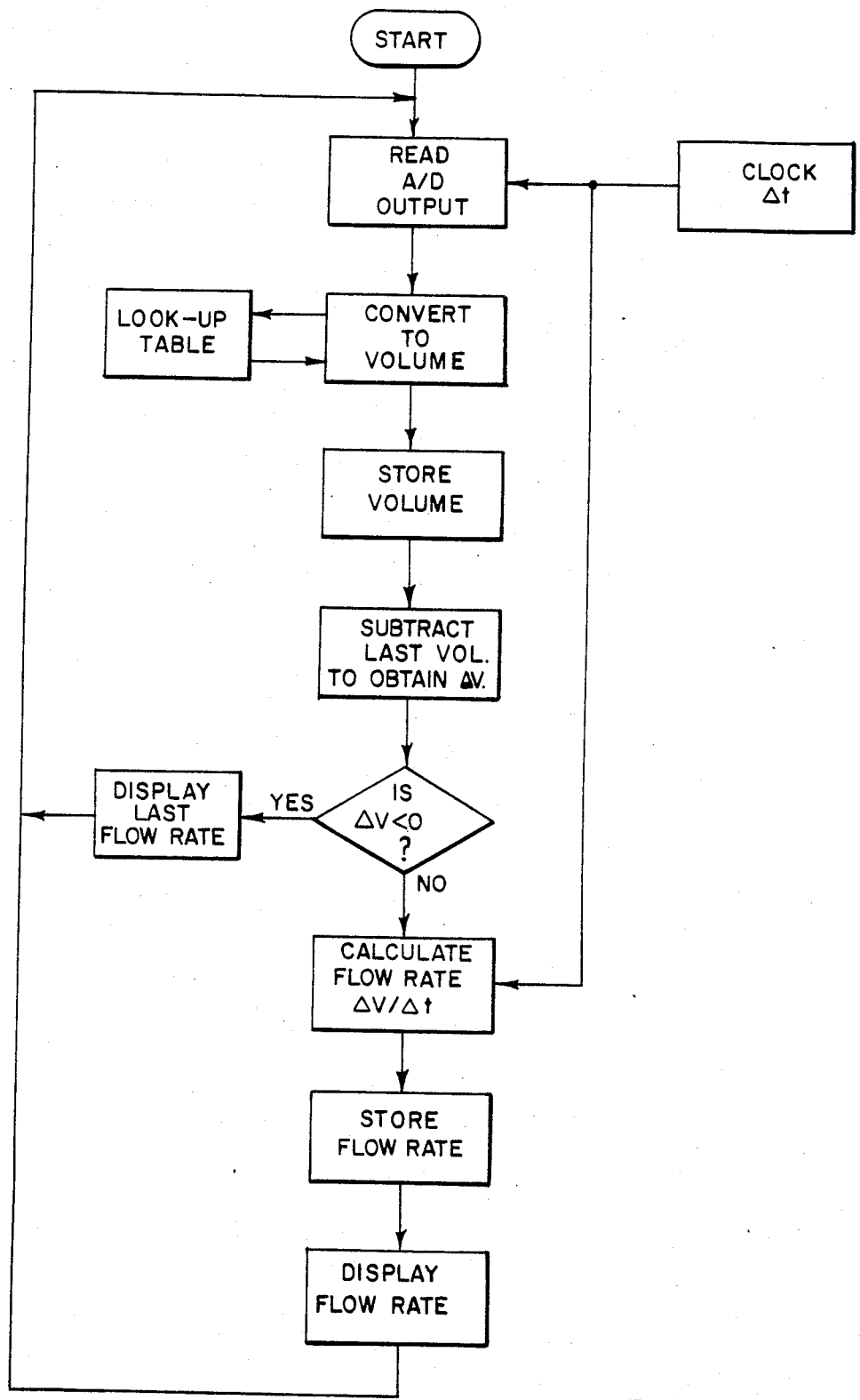
FIG. 3 is a flow chart of a program for the processor of the fluid flow meter of FIG. 1.

Referring to FIG. 3, the preferred processing technique employs a central processing unit 25 which has an internal clock which can generate a read signal at set intervals such as the microcomputer sold under the trade designation Intel 8051. The processing unit is programmed to await the signal from the internal clock to begin the portion of the program wherein the pressure signal is read and processed into the flow rate. The first step in this portion of the program is to generate an enable signal to be carried by an enable line 26 to the analog to digital converter 24. The analog to digital converter 24 would then convert the pressure signal from the transducer 22 into a digital signal which would be carried by a data bus 27 to the processing unit 25 where it is read.

The CPU 25 converts the digitized pressure signal into a volume using a look-up table. In the look-up table, the experimentally derived pressure-volume data is stored in associated memory addresses. The processor compares the input pressure value to the stored pressure values and stores the memory address of the experimental pressure value which is closest to the input pressure value. The processor then reads the volume from the memory address corresponding to the memory address of the closest experimental pressure value.

Returning to the mainstream of the flowchart in FIG. 3, the corresponding volume is stored in a third register. Each value stored in an address in the third register is separated in time from the immediately adjacent values by the time period between read signals from the internal clock. Therefore, the flow rate can be computed by taking the difference between two successive values and dividing it by the time period between the two values. For reasons to become apparent below, if the change in volume is negative, that is, if the volume in the container 11 decreases, it is desirable to disregard the change. In that case, the processor outputs the last flow rate and returns to await the next read signal.

If the change is zero or positive, the change in volume $\Delta V$ is divided by the time interval between read signals $\Delta t$ to yield the flow rate. The flow rate is then stored and displayed, and the processor returns to await the next read signal from the internal clock.

While any of a number of well known displays could be used, the preferred display is a strip chart recorder 30 to provide a histogram of the flow rate. The recorder 30 is interfaced to the CPU 25 by a digital to analog converter 31. When the CPU 25 reaches the display instruction in the program, it generates an enable signal which is carried by line 32 to the digital to analog converter 31 and enables the converter 31 to read the digital flow rate from the data bus 27. The converter 31 then converts the digital flow rate signal into an analog signal which is suitable for input to the recorder 30 via line 35. Also, the recorder 30 could be provided with an alarm which would light or sound whenever the flow rate was not within a preselected range.

The foregoing description adequately describes a container of the present invention. However, as liquid enters the container 11, the container 11 would eventually fill up and the liquid would exit the container via the vent opening 18 without other means provided. Therefore, in the preferred embodiment, the baffle 14 and the left hand portion of the exterior walls of the container 11 make up a second conduit which defines a second passageway 36. The second passageway 36 has a lower outlet opening 37 which opens into the cavity 15 above the lower opening 20 of the first passageway 19. The second passageway 36 also has an upper outlet opening 38 which is below the upper opening 21 of the first passageway 19 and opens to the exterior of the container. The upper outlet opening 38 is suitable to be connected to a drainage tube 40 which extends below the upper outlet opening 38 to a lower end (not shown). The lower end of the drainage tube 40 is below the lower outlet opening 37 and is connected to a drainage bag (not shown).

The second passageway 36 is provided so that the container 11 will automatically be partially drained. As liquid enters the container 11 and the level of liquid within the cavity 15 rises, the level of liquid within the passageway 36 will rise with it. Eventually, the liquid level within the passageway 36 will reach the level of the outlet opening 38. When this occurs, the liquid will exit the container 11 via the drainage tube 40 and create a suction which draws the level of the liquid within the cavity 15 down to the level of the lower outlet opening 37 by siphon action.

It should be noted that the area of the container 11 above the lower opening 37 and below the upper opening 38 is constant. This may be desirable in those applications where a derived equation is used to convert the pressure transducer 22 output signal into the flow rate to simplify the calculations. However, with the preferred processing technique of FIG. 3, this is irrelevant.

As the container 11 is drained by siphon action via the passageway 36, the liquid level within the cavity 15 will fall thereby causing the air pressure within the passageway 19 to fall. Any output attributable to the falling pressure would be meaningless and would be simply disregarded by an observer. However, in the preferred technique of FIG. 3, the processor disregards any negative changes in volume. It simply outputs the last flow rate and returns to await another read signal from the clock, as described above.

The container 11 can be inexpensively manufactured from injection molded polystyrene, thus, the cost of the container can be made low so that it is economical to dispose of the container after use. By making it economical to dispose of the container, the need for cleaning the container is ob- viated.

Many modifications and variations of the invention will be apparent to those skilled in the art. It is therefore intended that the scope of the invention is not to be determined by the description of the preferred embodiments, but by the claims which follow.

I claim:

1. An apparatus for providing a running indication of the dynamic flow rate of a bodily fluid by measuring the pressure exerted upon a column of air by the fluid as the fluid accumulates, comprising:
    an air pressure transducer responsive to the air pressure of the column of air for producing an output signal representative thereof, said air pressure transducer having a measuring port and a gauge port;
    a unitary container for receiving the flow of bodily fluid and for connection to the air pressure transducer, said container comprising:
        a chamber to receive the accumulating bodily fluid;
        inlet means for admitting the bodily fluid into the chamber;
        drainage means for siphoning accumulated bodily fluid from said chamber when said fluid reaches an upper level;
        a sealed substantially vertical measurement conduit for enclosing the column of air, said conduit sharing a wall in common with the chamber and being in communication with the chamber through an opening in the common wall at the base of the conduit;
        air pressure outlet means for providing sealed communication between the measuring port of the air pressure transducer and the measurement conduit above the upper level; and
        chamber pressure outlet means for providing communications between the gauge port of the air pressure transducer and the interior of the chamber above the upper level;
        wherein a dynamic flow rate of a bodily fluid into the chamber provides a corresponding dynamic air pressure at the air pressure outlet means to which the air pressure transducer is responsive; and
    processor means for converting the air pressure transducer output signal into a running indication of the instantaneous flow rate of the bodily fluid as the chamber fills to the upper level.

2. An apparatus as in claim 1 wherein the chamber pressure outlet means comprises a vent in the upper portion of the chamber so that the interior of the chamber and the gauge port of the air pressure transducer are in communication by both being exposed to the atmosphere.

3. An apparatus as in claim 1, wherein the drainage means includes a substantially vertical drainage conduit having a wall in common with the chamber and having an inside end in communication with the chamber through said common wall above where the measurement conduit is in communication with the chamber, said drainage conduit extending above said inside end and having an end opening outside the container below the air pressure outlet means, said outside end being sealable to a downwardly depending tube.

* * * * *